United States Patent [19]
Sanford et al.

[11] Patent Number: 5,228,988
[45] Date of Patent: Jul. 20, 1993

[54] COLUMN ANALYZER SYSTEM AND IMPROVED CHROMATOGRAPH COLUMN FOR USE IN THE SYSTEM

[75] Inventors: James R. M. Sanford, Vidor; Patrick M. Frank, Beaumont; Joseph H. Golias, Beaumont; William C. Jennings, Beaumont, all of Tex.

[73] Assignee: Helena Laboratories Corporation, Beaumont, Tex.

[21] Appl. No.: 779,186

[22] Filed: Oct. 22, 1991

Related U.S. Application Data

[60] Continuation-in-part of Ser. No. 733,714, Jul. 22, 1991, which is a continuation-in-part of Ser. No. 708,298, May 31, 1991, which is a division of Ser. No. 427,346, Oct. 27, 1989, Pat. No. 5,045,208.

[51] Int. Cl.⁵ ............................................. B01D 15/08
[52] U.S. Cl. ................................. 210/198.2; 210/656; 422/70; 436/161; 436/809
[58] Field of Search ...................... 210/198.2, 656, 635; 422/70; 436/161, 809; 55/386

[56] References Cited

U.S. PATENT DOCUMENTS

| | | | |
|---|---|---|---|
| 3,508,880 | 4/1970 | Hrdina | 210/198.2 |
| 3,518,874 | 7/1970 | Hrdina | 210/198.2 |
| 3,922,223 | 11/1975 | Burkhartsmeier | 210/198.2 |
| 3,925,207 | 12/1975 | Scriba | 210/198.2 |
| 3,926,809 | 12/1975 | Jones | 210/198.2 |
| 3,954,617 | 5/1976 | Ishimatsu | 210/198.2 |
| 4,079,009 | 3/1978 | Seller et al. | 210/198.2 |
| 4,341,635 | 7/1982 | Golias | 210/198.2 |
| 4,604,198 | 8/1986 | Dailey et al. | 210/198.2 |
| 4,766,082 | 8/1988 | D'Autry | 210/198.2 |
| 5,045,208 | 9/1991 | Sanford et al. | 210/198.2 |

FOREIGN PATENT DOCUMENTS 0288425 10/1988 European Pat. Off. .

Primary Examiner—Stanley S. Silverman
Assistant Examiner—Neil M. McCarthy
Attorney, Agent, or Firm—Spencer, Frank & Schneider

[57] ABSTRACT

An analyzer system for automatic column chromatography includes chromatographic columns which are mounted in a rack. A drop removal mechanism system shakes the rack to transfer the last drop of eluate from the tip of a chromatographic column to a receptacle below the tip before the column is repositioned over another receptacle and another fluid or operation is introduced into the column. This prevents one eluate from contaminating another. The chromatographic column may have an upper end which is sealed by a foil member. During use, the foil member is ruptured by lowering a pressure cylinder with a seal-punching head against it. The pressure cylinder, which is part of the pressure tip unit, is then withdrawn so that fluid can be introduced into the column via the ruptured foil member. The pressure tip unit is then lowered into sealing engagement with the column so that pressure can be applied via a bore in the pressure cylinder. The column may also have a tip portion which is originally sealed by a removable cap. The rack has a plate with aperture that is configured to receive the tip portion of the column and to provide a bearing surface for a decapper member which removes the cap. This decapper member is lowered through the aperture, and the bearing surface forces it toward the tip portion so that the cap can be pushed off. After the chromatographic columns have been used, they can be regenerated for re-use without removing them from the rack.

6 Claims, 11 Drawing Sheets

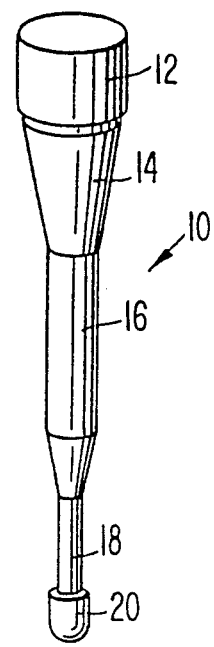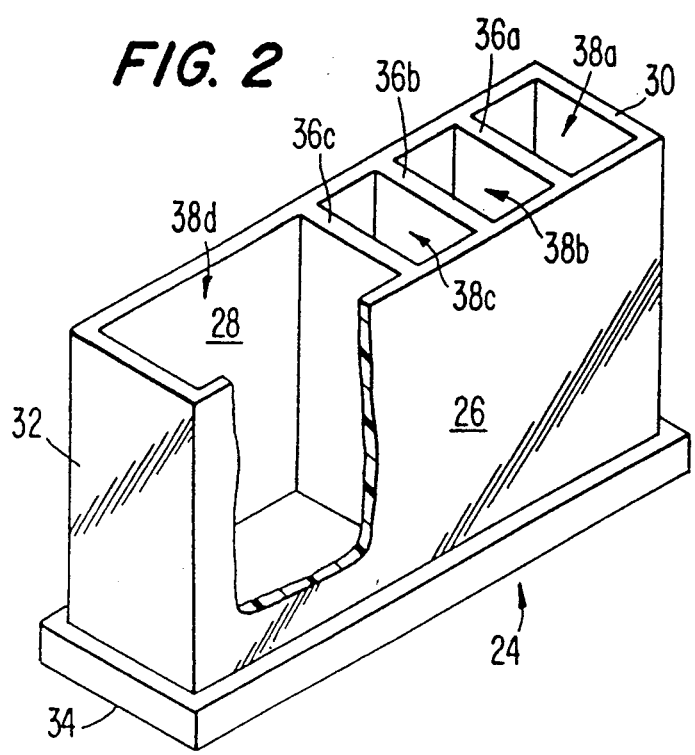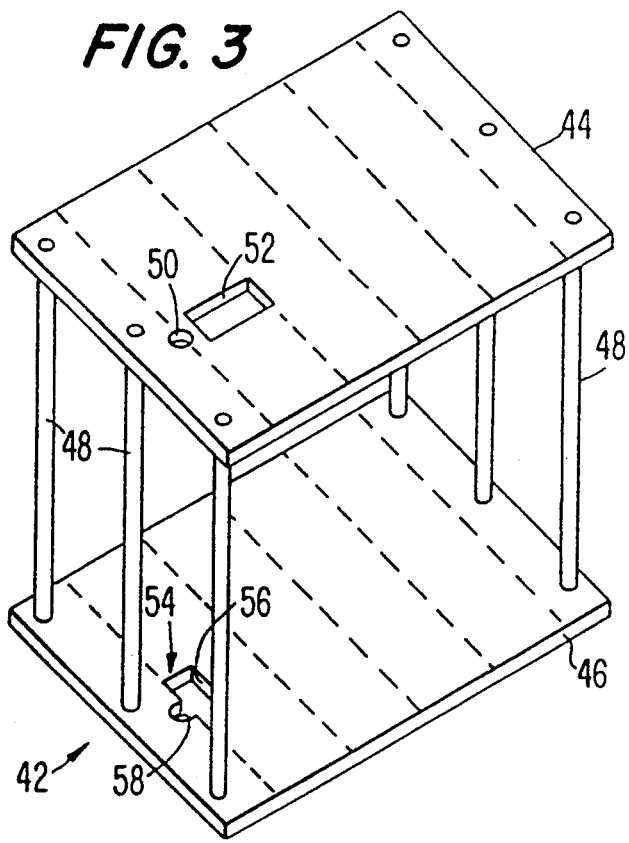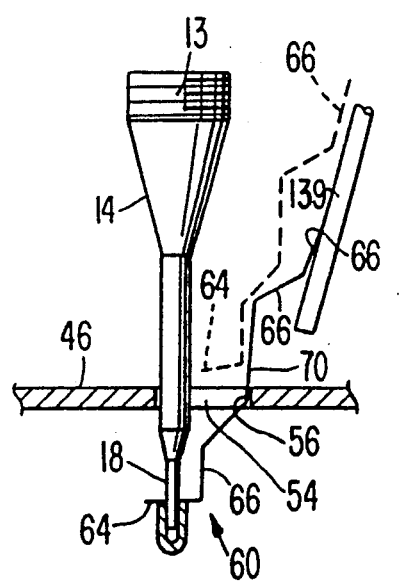

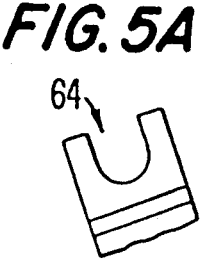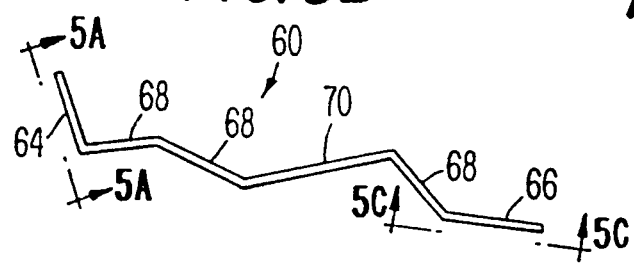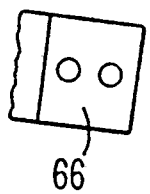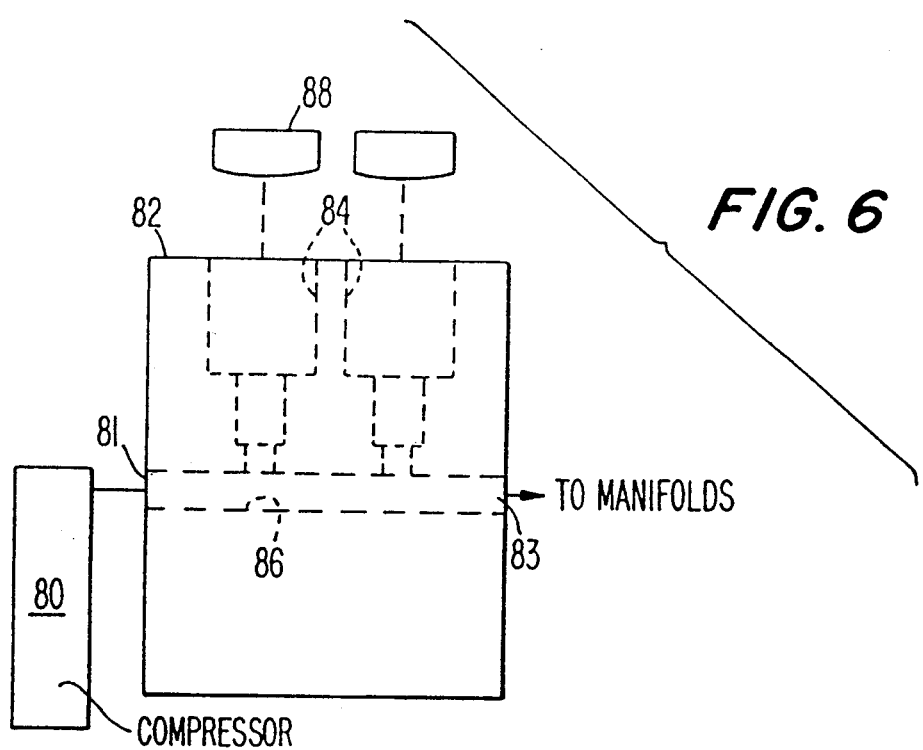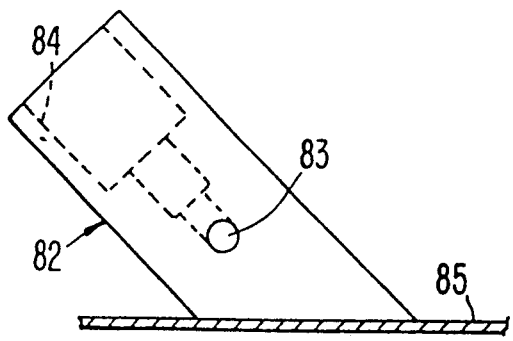

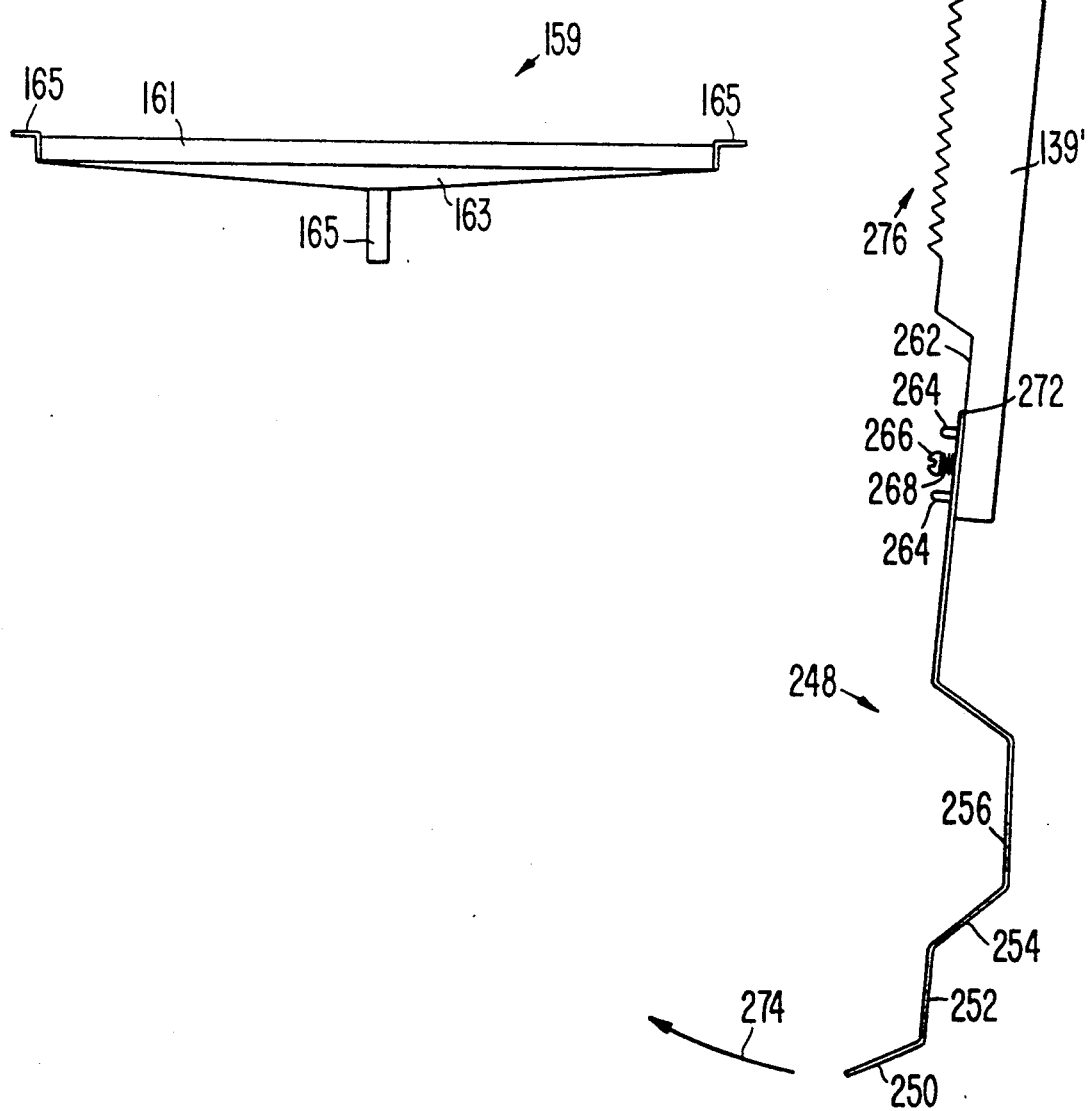

COLUMN ANALYZER SYSTEM AND IMPROVED CHROMATOGRAPH COLUMN FOR USE IN THE SYSTEM

CROSS-REFERENCE TO RELATED APPLICATIONS

This is a continuation-in-part of application, Ser. No. 07/733,714, filed Jul. 22nd, 1991, which application is a continuation-in-part of application, Ser. No. 07/708,298, filed May 31st, 1991, which application is a division of application, Ser. No. 07/427,346, filed Oct. 27th, 1989 now U.S. Pat. No. 5,045,208. The disclosures of these parent applications are incorporated herein by reference.

BACKGROUND OF THE INVENTION

This invention relates to column chromatography and, more particularly, to an improved column analyzer system which provides for automatic column chromatography and automatic optical density processing.

Column chromatography, using chromatographic media contained in small disposable columns (often called microchromatography), is a well-known technique utilized as part of clinical chemistry for analyzing various constituents of biological fluids, such as blood. These media may be prepared from cellulose, agarose, silica, and various plastics, and typically utilize the presence of attached groups which are ionic (cation and anion), hydrophobic, or affinity specific in character. For example, Helena Laboratories Corporation, the assignee of the present invention, has marketed equipment and accessories for column chromatography as well as photometers or optical readers. Patent literature relating to column chromatography includes, for example, U.S. Pat. No. 4,341,635, issued Jul. 27th, 1982 to Tipton Golias and assigned to Helena Laboratories Corporation (as well as the prior art cited therein), and there is commercially available equipment relative to automating one or more aspects of column chromatography. For example, at least one machine has been marketed prior to the present invention which automates the introduction of fluids into a chromatographic column, and the collection of the eluates from the column. Such equipment also provides for the processing of a plurality of chromatographic columns which are arranged in an array or matrix within the equipment.

The prior art, however, suffers from numerous disadvantages and shortcomings relative to the safe, accurate and expeditious chromatographic processing and subsequent optical density readings.

For example, according to the prior art, the eluate solutions are collected in a series of cuvettes, one cuvette for each eluate solution or fraction. Thereafter, the cuvettes are sequentially processed in an optical reader. This technique is time consuming, permits errors in identification of the cuvettes and exposes the technician handling the cuvettes to biological hazards such as HIV virus which may be carried in the blood specimens. The equipment which automates the processing of columns has heretofore discharged the eluates into a series of test tubes, and then the technician or operator of the equipment must manually transfer the test tubes to a reader.

While extremely high pressure liquid chromatography (HPLC) is well known, and while pressurized chromatography is known based upon the aforementioned Golias U.S. Pat. No. 4,341,635, we have discovered that a constant low pressure greatly enhances liquid chromatography. Prior to the present invention, however, constant low pressure liquid chromatography was not available.

SUMMARY OF THE INVENTION

The present invention overcomes the shortcomings of the prior art by providing a new and improved column analyzer system and method.

The column analyzer system of the present invention provides for the automated processing of an array of chromatographic columns, including the rupturing of foil seal members from the columns using pressure tip units with seal-punching heads and the removal of caps from the columns using spring members which are deflected by bearing edges provided by the racks in which the columns are mounted, without technician intervention solutions.

The present invention further provides for automatically shaking loose the last drop of eluate from a column to avoid transferring it to the wrong receptacle.

The present invention further provides for an improved chromatography column whose top end is sealed by a foil member.

BRIEF DESCRIPTION OF THE DRAWINGS

The foregoing objects and advantages of the present invention, together with other advantages which may be obtained by its use, will become more apparent by reading the following detailed description of the invention taken in conjunction with the drawings.

In the drawings, wherein like reference numerals identify corresponding components:

FIG. 1 is a perspective illustration of a chromatographic column;

FIG. 2 is a perspective illustration, partially broken away, of a cuvette;

FIG. 3 illustrates, in perspective view, a rack for supporting a plurality of chromatographic columns;

FIG. 4 is a side view, partially in section, illustrating an embodiment of the apparatus for removing the caps from the chromatographic columns;

FIG. 5, comprising FIGS. 5A, 5B and 5C, illustrates the cap removal means in FIG. 4 with elevation views of each end thereof and with an edge view thereof;

FIGS. 6 and 7 illustrate the system for supplying constant, low pressure including a pressure regulator;

FIG. 21, comprising

FIG. 24 is a side view illustrating the modified embodiment of the cap removal means mounted on an actuating mechanism; and FIG. 25 is a front plan view of a tray that can be used during column regeneration.

DETAILED DESCRIPTION OF THE INVENTION

Figure 8:
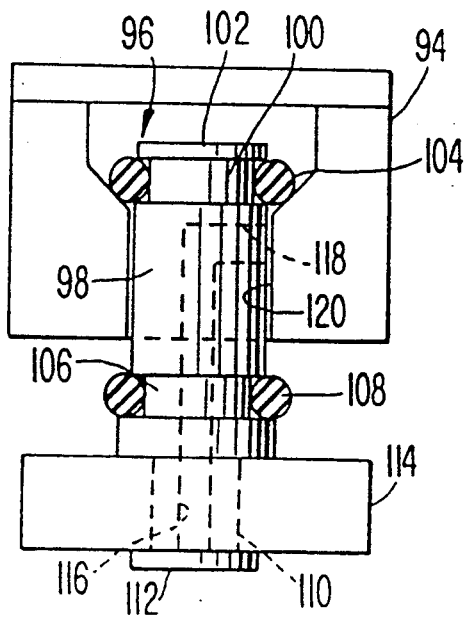
FIG. 8 illustrates an embodiment of the pressure tip associate with a single chromatographic column in a first position disengaged from a column.

With reference to the drawings, FIG. 1 illustrates a chromatographic column 10 which includes an upper end or cover 12 threadingly engaged onto the body portion of the column. The body portion of the column includes a downwardly and inwardly tapering reservoir portion 14 communicating with a barrel portion 16, which barrel portion contains a chromatographic medium. 18 which is covered by a removable cap 20. The column 10 as described and illustrated, including a threadable cover 12 (threads 13 are shown in FIG. 4), is conventional.

During liquid chromatography, it has been conventional, prior to the present invention, for the eluates to be discharged into a series of cuvettes or a series of test tubes. When test tubes are used, the contents may subsequently be transferred into cuvettes, depending on the equipment employed. The body of a test tube tends to interfere with the optical density reading, and a cuvette, with its generally flat walls, avoids this problem. However, prior to the present invention, each of the eluates from a chromatographic process have been collected in discrete cuvettes leading to the risk of errors in the processing of the individual cuvettes.

The present invention provides an improved cuvette means 24 which provides for the collection of all of the eluates from a single column within separate cells of a single cuvette means. With reference to FIG. 2, the cuvette means 24 is a generally rectangular container having opposed, parallel, spaced-apart side walls 26, 28, and opposed, spaced-apart parallel end walls 30, 32 oriented perpendicular to the side walls. The side walls and end walls of the cuvette means are mounted on a base 34, and the side walls and end walls, together with the base, define a rectangular container which is open at the top and closed at the bottom.

By way of example, but not by way of limitation, the cuvette means may include four separate cells. Three interior walls 36a, b, c extend between the side walls 26, 28, with the interior walls being generally parallel to the end walls 30, 32. The cuvette means thus defines four discrete cells 38 a, b, c, d, respectively. Each cell is defined by the base 34, the side walls 26, 28, and two additional walls. In the case of cell 38a, the two additional walls are walls 30 and 36a; for cell 38b, the two additional walls are walls 36a and 36b. The two additional walls which define cell 38c are interior walls 36b and 36c. The two additional walls which define cell 38d are walls 36c and 32. It should be noted that cells 38 a, b, c are of generally equal size and are substantially smaller than cell 38d for reasons which will be hereinafter explained.

Referring to FIG. 3 a rack 42 is provided for supporting an array of columns. The rack includes upper and lower plates 44, 46, respectively, supported and maintained in spaced-apart relationship by a plurality of cylindrical rods 48. In the present embodiment of the invention, the upper and lower plates support 50 columns 10 in a 5×10 array. The upper plate 44 is provided with a series of circular apertures 50 of a size and shape to receive the barrel 16 of the column 10. Adjacent each circular aperture is a rectangular aperture 52 to accommodate the automatic column cap removal means which will hereafter be explained and to provide access to the cuvettes beneath rack 42. The lower plate 46 includes a plurality of apertures 54 which are generally rectangular in configuration. Each generally rectangular aperture 54 includes opposed short walls, a first longer wall interconnecting the short walls, and a second wall 58 opposed form the longitudinal wall 56, which second wall includes a cutout portion that is generally configured as three-quarters of a circle. The diameter of the cutout portion is configured to support the lower end of the barrel 16 of the column, and is aligned under the circular aperture 50 in the upper plate. The longitudinal wall 56 is a bearing surface for the automatic cap removal. In FIG. 3, only a single set of apertures in plate 44 is illustrated although 50 such sets, in a 5×10 array are contemplated. Similarly, only a single aperture 54 is illustrated in plate 46 although a 5×10 array is contemplated. The rack is positioned at a first station in the apparatus of the present invention. The apertures 54 permit access to the cuvettes under rack 42.

After the chromatographic columns are loaded into the rack and placed in position at the first station in the apparatus of the present invention, means are provided for automatically removing the cap 20 from the lower end of each column. FIG. 4 illustrates two positions of the cap removal means, an intermediate position illustrated by dashed lines and an active position illustrated by solid lines. It will be apparent that upper plate 44 has been omitted from the drawing in FIG. 4. The automatic cap removal means 60 is an elongated, thin, stainless steel spring strip extending generally vertically (or, more exactly, at 5.5° angle from the vertical) through the rectangular portions of the apertures 52, 54 in the upper and lower plates of the rack 42. As also illustrated in FIG. 5, the elongated, thin, steel spring includes a fork portion 64 at the lower end, an apertured upper end 66 for attachment to an actuating mechanism 139, and a series of intermediate portions 68 and 70 therebetween, one of which intermediate portions bears against the bearing surface wall 56 as the cap removal means is moved vertically downward within the rack 42. The cap removal means is attached to actuating mechanism 139 by screws (not shown) extending through the apertures in end 66. As the actuating mechanism moves the spring 60 vertically downward, from a rest position above the column and past the intermediate position shown in dotted lines, the spring 60 engages the longitudinal wall 56 in the lower plate 46. The continued downward movement of the spring against the bearing surface 56 urges the fork means toward the left to the active position illustrated in solid lines in FIG. 4, and the tip 18 of the column is engaged between the fork tines. After portion 70 reaches bearing surface 56, the continued downward movement of the spring forces the cap 20 downwardly until the cap is free of the column. The cap will, in practice, be retained in the first cell 38a of the cuvette means. Thereafter, the cap removal means is withdrawn vertically upwardly.

Means are provided for automating the column chromatography processing including such steps as applying hemolysate to the sample, agitating the column, running a buffer through the column, thereafter adding the sample to the column, adding the reagent to the column, etc. In general terms, this automatic technique is part of the prior art. However, the present invention includes certain features which ar not found in the prior art. One of the these features is the provision of constant, low pressure for the chromatographic columns which are being processed. The pressure system will now be explained.

Referring to FIGS. 6 and 7, the pressure system includes a compressor 80 for providing constant air pressure to an input port 81 of a regulator 82. The regulator 82 also includes an output port 83.

The regulator 82 includes two pressure relief bores 84, each of which is generally T-shaped in cross section, and air from the compressor 80 flows through the input port 81, through the main conduit 86 and through the output port 83 of the regulator. The two relief bores 84 are provided to permit operation of the regulator at two different constant pressures. For this purpose, each relief bore is provided with a projectile shape plunger 88, the plunger in one relief bore being of a different weight than the plunger in the other relief bore. In addition, each relief bore 84 may be selectively closed at the exterior surface thereof such that only one relief bore will be in use at any given time. FIG. 7 illustrates the orientation of the regulator 82 when it is mounted on a chassis 85 during use. It will be noted that relief bores 84 are positioned at an angle relative to the vertical axis. In operation, with the plungers mounted within the respective relief bores and with one of the relief bores open and the other closed, if the air pressure through the conduit exceeds a threshold as determined by the weight of the plunger associated with the open relief bore, the air will move the respective plunger upward opening a fluid flow path through the relief bore thus providing for a bleed of air pressure. When sufficient air pressure bleeds out through the relief bore, the plunger drops back to seal the relief bore from the main conduit. Selector valves (not illustrated) permit pressure relief bores 82 to be selectively sealed from main conduit 86. Positioning the plungers in bores 84 at an angle to the vertical facilitates movement of the plungers.

According to the principles of the present invention, a low but constant air pressure should be maintained at the output port 83. The pressure that is selected should be high enough to increase the flow rate through the chromatographic columns but not high enough to compress the resin beds of the columns or to allow the fluid in the beds to be expelled. The optimum pressure will depend on the properties of the columns and the resin matrixes therein. For example, a pressure of about three inches of water has been found to be appropriate for columns with a cellulose resin available from Whatman Incorporated, while a pressure of about eight inches of water has been found to be appropriate for columns with "Emberlite" CG50 resin, available from Rohm & Haas. The weights of the two plungers may be selected such that one plunger is sufficiently light so as to permit a constant air pressure equivalent to three inches of water (for example), and the second plunger is slightly heavier, thus permitting a constant air flow pressure at eight inches of water (for example). It should be further appreciated that the low pressure employed is not limited to the range of three-eight inches of water, which is merely illustrative. Less than three inches or more than eight inches may be utilized as the constant low pressure, depending on the particular chromatographic columns that are used, while achieving the objective of the present invention.

Experience has shown that regulator 82 can be simplified if a quality piston compressor is used for compressor 80. Screw-adjustable needle valves (not shown) can then be used in lieu of plungers 88 to provide air at a fairly constant low pressure to the columns.

Referring next to FIG. 8, it should be remembered that the columns are provided in an array, heretofore described as a 5 × 10 array, namely, 10 chromatographic columns in each of 5 rows. The output from the pressure regulator 82 is coupled through tubes 93 (see FIG. 17) to each of five manifolds 94, each associated with one row. Each manifold 94 is connected to a pressure tip system of the present invention for providing the desired pressure to each of the chromatographic columns while, at the same time, preventing leakage of air if less than a full array of columns is being processed by the system. The pressure tip system, as illustrated in FIG. 8 in the absence of a chromatographic column, includes an upper block or manifold 94 having a conduit 96 therethrough in fluid communication through tube 93 with the output 83 of the pressure regulator. Mounted partially within the block 94 is an elongated pressure cylinder 98, of generally circular cross section, having three reduced diameter circumferential recesses machined therein. Specifically, cylinder 98 has an upper grove or recess 100 machined therein, the upper groove positioned inwardly of a flange 102. An O-ring seal 104 is positioned within the groove 100. A second groove 106 is provided intermediate the two ends of the cylinder 98, and an O-ring 108 is positioned in the second groove 106. A third groove 110 is provided in the cylinder adjacent the second end and is spaced inwardly therefrom such that a lower flange 112 is provided at the second end of the cylinder 98, and a flexible, foam gasket 114 is provided and mounted in the groove 110, the foam gasket 114 being retained by the flange 112. The cylinder 98 has a longitudinal bore 116 extending through the flange 112 and through the body of the cylinder, the bore 116 extending along the longitudinal center line of the cylinder of the upper groove 100. A transverse bore 118 is provided generally perpendicular to the longitudinal bore 116 and intersecting the longitudinal bore 116 at the end thereof inwardly of the upper groove 100. The longitudinal bore 118 is in fluid communication with a circular passageway 120 which is provided within the block 94.

In the absence of a chromatographic column, the pressure tip system is positioned as illustrated in FIG. 8 such that the weight of the pressure tip system pulls the cylinder vertically downwardly causing the O-ring 104 to seal the top of the passageway 120 from the conduit 96, thus preventing the air flow from entering the vertical passageway 120. A spring (not illustrated) can also be used above flange 102 to urge pressure cylinder 98 downward. Thus, O-ring 104 functions both as a seal and also as a retainer which engages the flange 102 and prevents the cylinder mechanism 98 from dropping downwardly out of the passageway 120 of the block 94.

Figure 9:
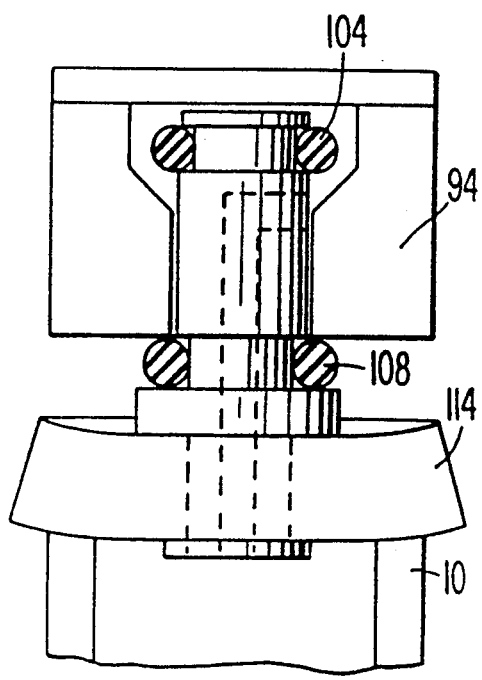
FIG. 9 illustrates the pressure tip associated with a single column in the engaged position.

During the operation of the system of the present invention, the entire pressure system is movable such that cuvettes may be placed in the chassis, and chromatographic columns may be placed in frame 42 within the chassis. Thereafter, the pressure system is moved into position relative to the chromatographic columns and lowered into position such that for each chromatographic column mounted in the rack 42, the top end of the column 10 engages the underside of the foam gasket 114 and pushes upward on the foam gasket such that the foam gasket, while still mounted in the groove 110, moves the cylinder 98 upwardly until the O-ring 108 seals the vertical passageway 120 at the bottom of the block 94. This is illustrated in FIG. 9. Simultaneously pressure between the top of the column 10 and the underside of the foam gasket 114 provides an air-tight seal at the top of the column. Lastly, the vertical upward movement of the cylinder 98 moves the upper O-ring 104 clear of the top of the passageway 120. Thus, air pressure through the conduit 96, which is in communication with the output port 83 of the pressure regulator 82, flows through the conduit 96 (for each pressure tip unit), downwardly through the passageway 120 and through the horizontal bore 118 and the vertical bore 116 and thereafter into the top of the chromatography column. A pressure system such as illustrated in FIGS. 8 and 9 is associated with each location in the array of columns.

Thus, it may be appreciated that if a full array of columns is being processed, each column presses upwardly on its respective foam gasket 114 to permit air pressure to flow into the top of the chromatographic column whereas in each position within the array which is characterized by the absence of a chromatographic column, the pressure system remains in the position of FIG. 8, and no air enters the cylinder 98 associated therewith.

Figure 10:
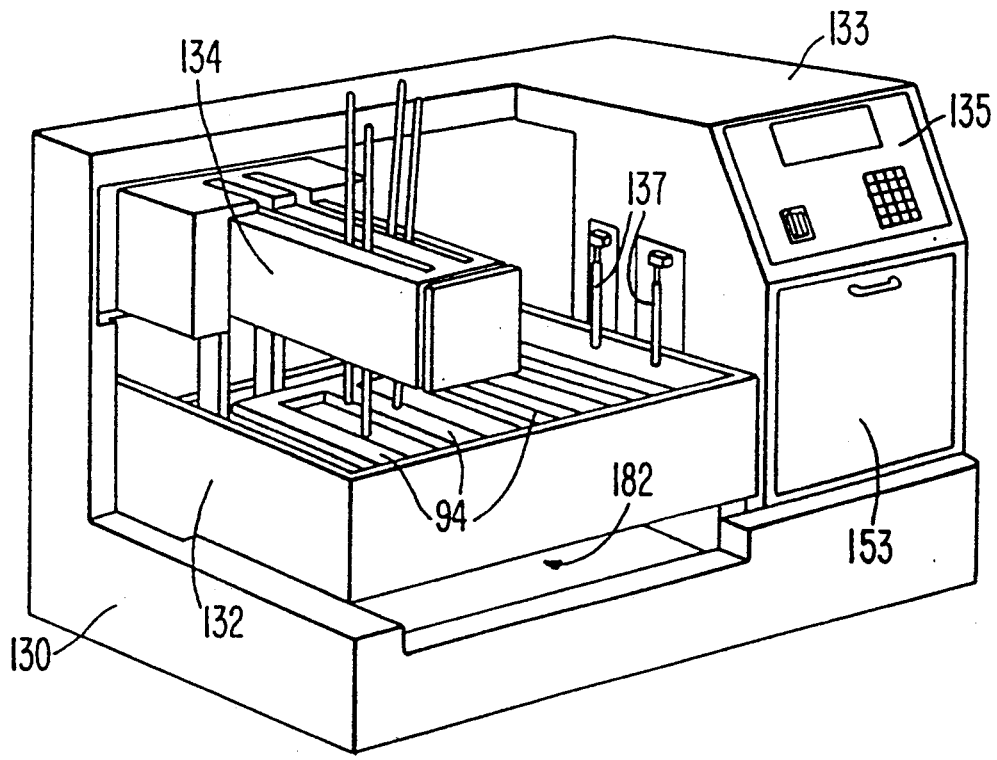
FIG. 10 illustrates, in perspective view, the apparatus of the present invention.

Referring next to FIG. 10, a perspective illustration of the apparatus of the present invention is illustrated. The apparatus of the present invention includes a chassis or frame 130. The frame or rack 42 for the chromatographic columns is mounted within a housing 132 to the frame. FIG. 10 also illustrates the five manifolds 94 positioned above the rack 42, the five manifolds or blocks extending from the front to the rear of the housing 132. The cuvettes are positioned below the housing 132 as will be described hereinafter. At its right side, with respect to FIG. 10, the apparatus includes a control housing 133 with a control panel 135. Although not shown, a printer is disposed in control housing 133 to print out test results, and a sample rack is mounted on the front wall of housing 132 to hold small cups containing specimens that are to be transferred to the chromatographic columns.

Above the housing 132, a horizontal support block 134 is mounted for movement laterally, i.e., in the "X" direction. Thus, the block 134 moves left and right. Mounted within the block are three discharge needles 136, 137, and 138, along with actuating mechanism 139 (see FIG. 17). The needles and actuating mechanism move as a group in the "Y" direction, i.e., forwardly and rearwardly of the block 134. They also move in "Z" or vertical direction. Syringe pumps 137 are mounted on housing 133 and connected via tubing, not illustrated in FIG. 10, to two of the needles. The syringe pumps transfer the samples and various fluids known in the art to the chromatographic columns. A tray 142 for supporting the cuvettes is slidably mounted under the housing 132 (see FIG. 11).

Figure 11:
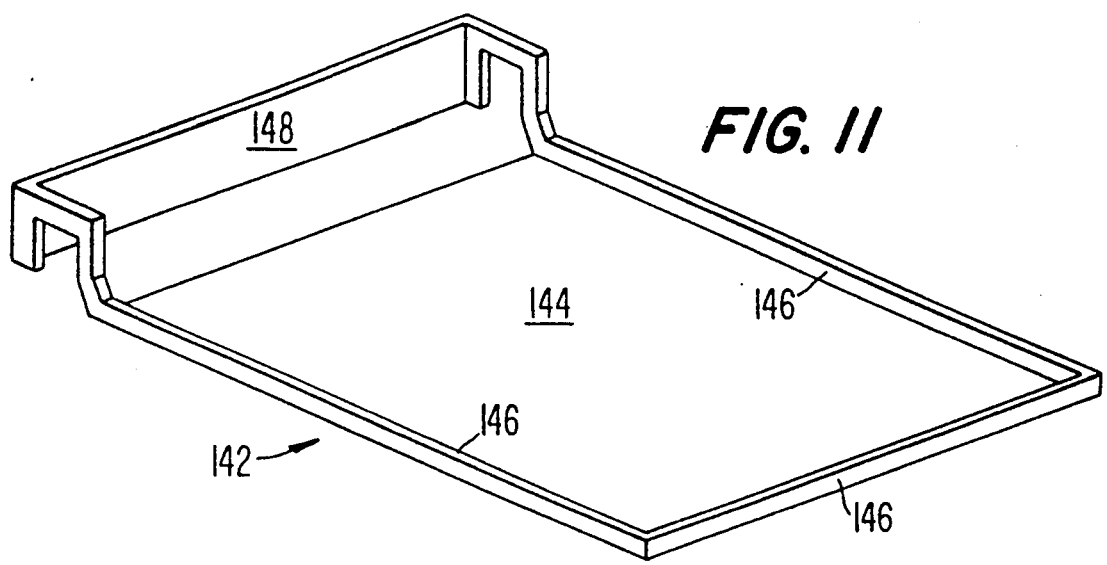
FIG. 11 illustrates, in perspective view, a tray for supporting the cuvettes.

FIG. 11 illustrates, in perspective, the tray 142 for the cuvettes, the tray including a generally flat surface or floor 144 upon which the cuvettes are placed, the floor being provided with guide rails 146 on three sides thereof. A handle 148 is provided on the tray for movement of the tray of cuvettes into and out of the apparatus of the present invention. The tray of cuvettes has been removed from FIG. 10 for the purposes of clarity and ease of illustration.

Experience has shown that technicians who place the cuvettes 24 on tray 142 may occasionally, through carelessness, set the base 34 (see FIG. 2) of one cuvette on top to the base 34 of another cuvette near its edge, thus tilting the cuvette. Although not shown, this problem can be eliminated by attaching wedge-shaped spacers at the centers of the side walls 26 and 28 of the cuvettes and by altering the end walls 30 and 32 so that they have wedge-shaped cross-sections, which, in effect, provides spacers at the ends.

Figure 12:
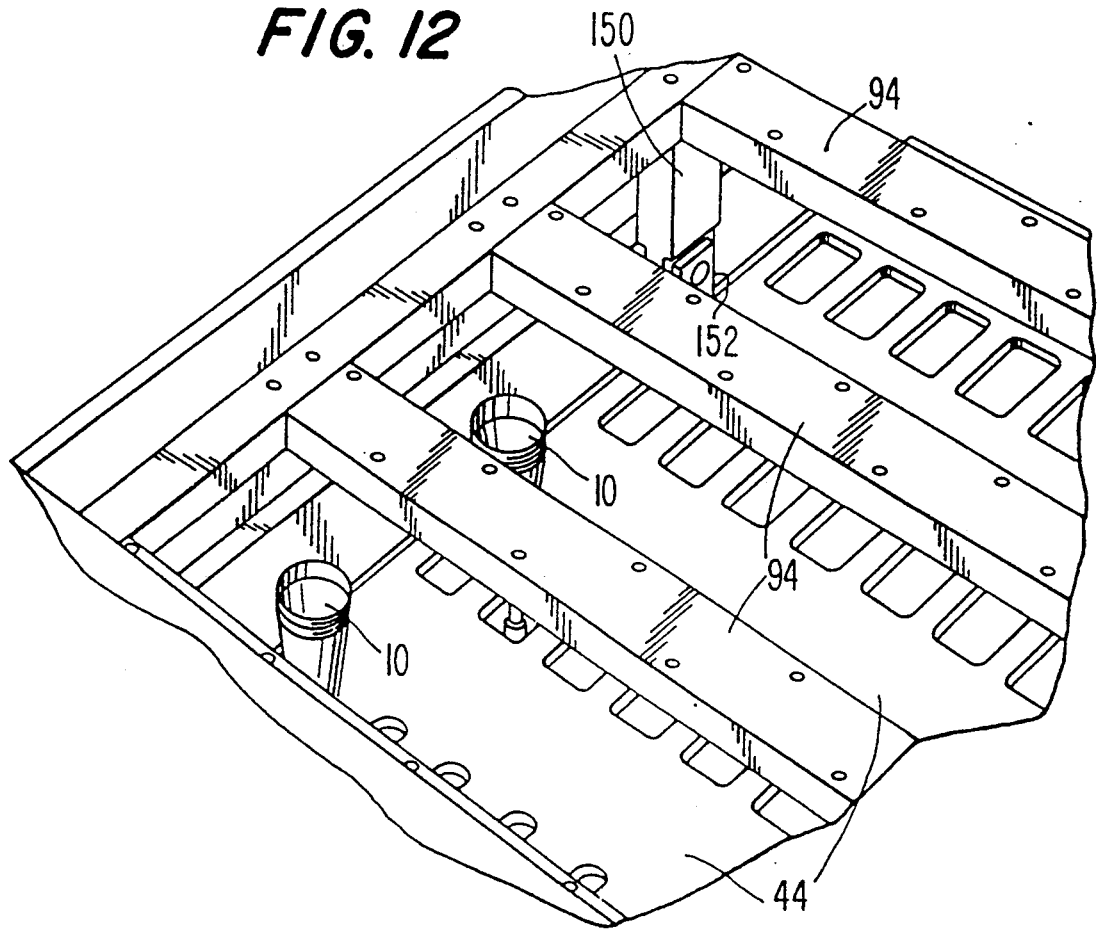
FIG. 12 illustrates a portion of the top of the column rack and a portion of the manifold system in a disengaged position as seen from the back of the apparatus.

FIG. 12 illustrates, in perspective form, a rear view portion of the apparatus of the present invention, including the movable pressure tip system for engagement with the chromatographic columns. In FIG. 12, three of the manifolds of blocks 94 are visible, as is the upper plate 44 of the rack 42 with two chromatographic columns 10 in place, one in each of two rows. At the upper right-hand corner of FIG. 12, part of an L-shaped link 152 (also see FIGS. 15 and 16) is visible. It is pivotably connected to a leg 150 which is attached to the manifolds 94. Four such legs 150 are provided to support the manifolds, and each is pivotably connected to a respective link 152. When the system is in the position illustrated in FIG. 12, the links 152 are disposed in an upright position and the manifolds 94 are in their raised positions, offset from the columns 10. In this raised and offset position, the needles 136, 137, 138 can access the tops of each of the chromatographic columns so that resuspension, separation, regeneration, or other fluids may be introduced therein or so that resuspension or other operations can be conducted.

Figure 13:
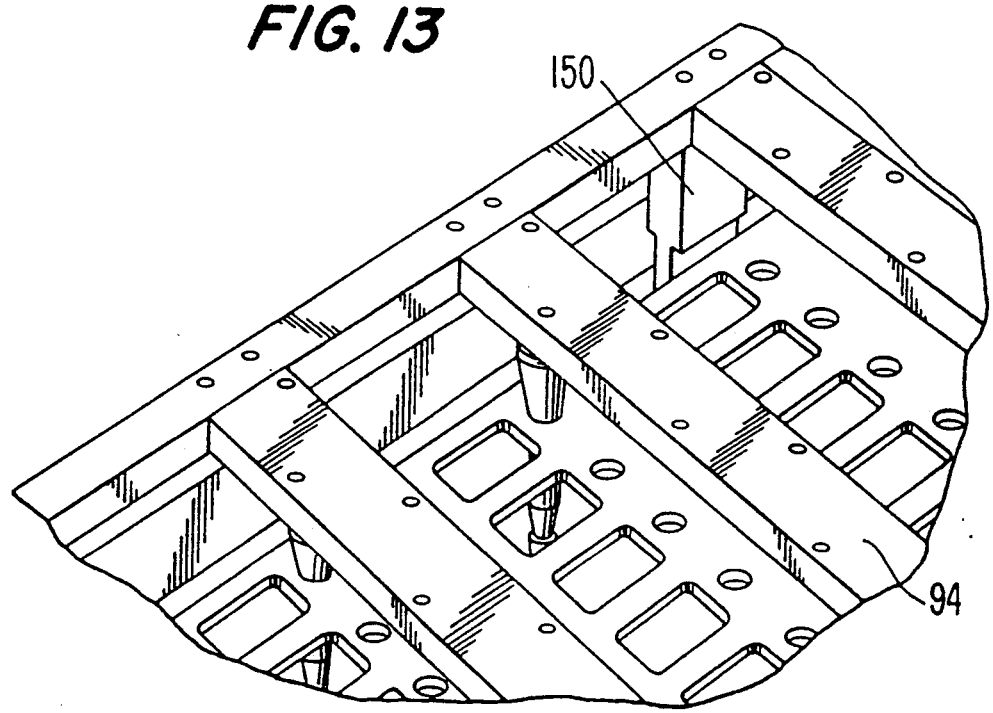
FIG. 13 illustrates the top of the column rack and a portion of the manifold system of FIG. 12 in an engaged position.

FIG. 13 is a perspective illustration similar to FIG. 12 except that the links 152 have been rotated and the manifolds are now in their lowered position. When the links 152 are rotated from their upright positions, there is a downward swinging movement of the manifolds 94 such that the manifolds 94 move above the columns 10 and the pressure tip system of FIGS. 8 and 9 makes contact with the tops of the columns.

Figure 14:
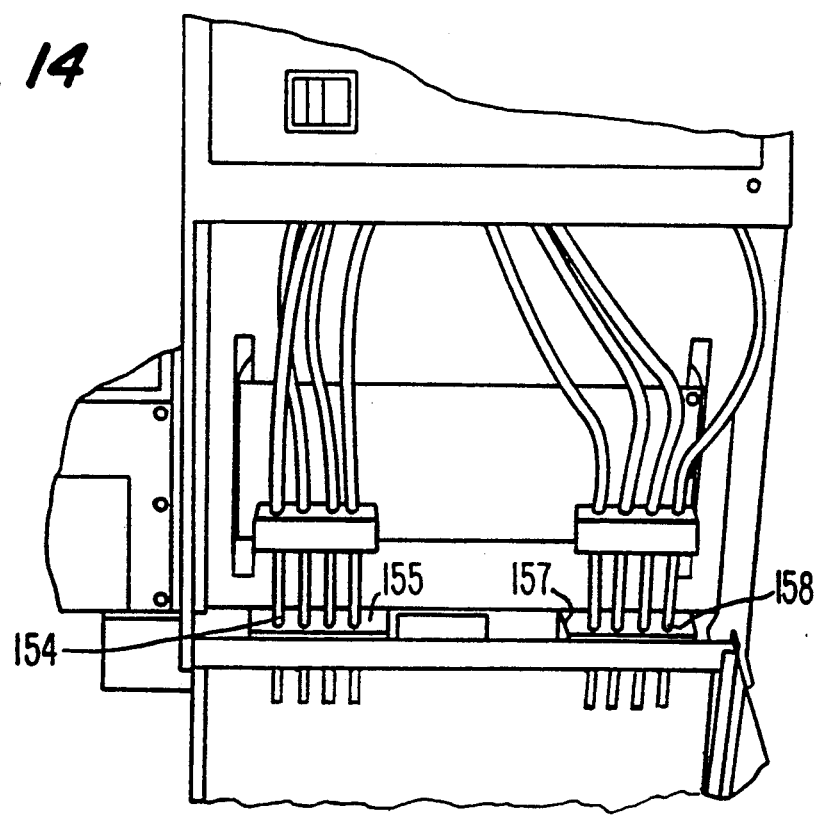
FIG. 14 is a partial front illustration with the door of the apparatus removed.

FIG. 14 illustrates an enlarged, partial front elevation view of the apparatus of the present invention with the door 153 of control housing 133 (FIG. 10) open. In this position, a first group of mixing needles 154 is illustrated. There are four such needles, which can be associated with any cell of a cuvette. After chromatographic separation, the cuvette is moved to the right in FIG. 14 by a stepping motor and is held in position underneath the needles 154 such that the fluid within each cell may be thoroughly mixed. The cuvette is then moved further to the right in FIG. 14 to be scanned by an optical reader 156 (see FIG. 17). After scanning by the optical reader 156, the cuvette advances further to the right under a second group of needles 158 which remove fluid from the cuvette cells.

It was previously indicated that cuvette cell 38d is larger than the other three cuvette cells. This is because in column chromatography, it is common to collect eluates and, in a separate container, dilute a second sample (e. g., of blood or other biological fluid) such that comparative optical density readings may be taken for providing a reference standard for the purpose of quantifying purified fractions thereof relative to the standard. This technique is, of course, well known.

Figure 15:
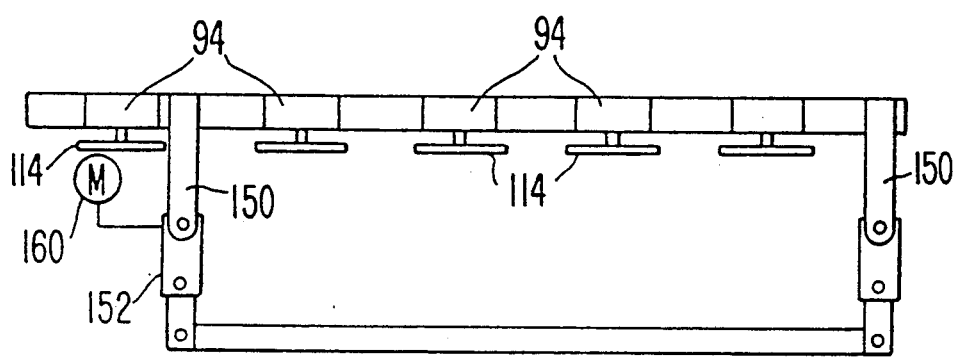
FIG. 15 is a diagrammatic illustration of the motor and linkage for positioning the manifold system in the disengaged or upper position.

FIG. 15 illustrates, in diagrammatic form, linkage and a motor 160 for moving the manifold system to the raised position, in which the manifold system is retracted relative to the tops of the individual chromatographic columns such that reagents, and samples and the like may be introduced therein. As will be apparent, the L-shaped links 152 are in their upright position in FIG. 15.

Figure 16:
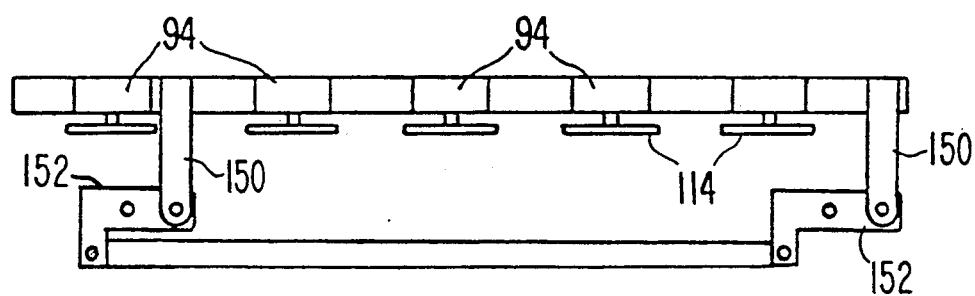
FIG. 16 is a diagrammatic illustration of the motor and linkage for positioning the manifold system in the engaged or lowered position.

FIG. 16 illustrates, diagrammatically, the linkage and motor system of FIG. 15 in the engaged position, illustrating the 90° rotation of the aforementioned links 152. It should be noted that while FIGS. 12 and 13 provide a rear perspective illustration, FIGS. 15 and 16 provide a front elevation diagrammatic illustration.

Figure 17:
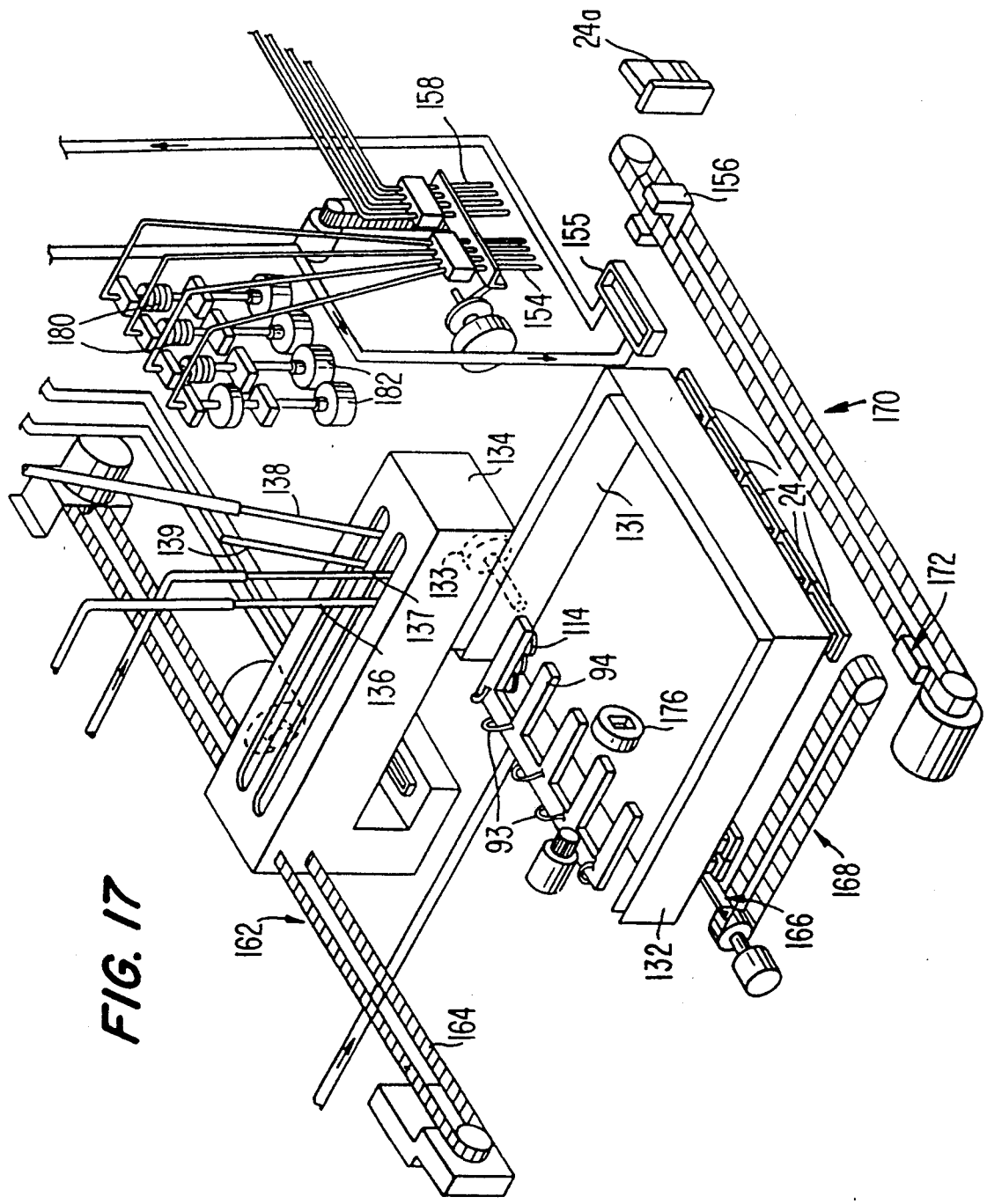
FIG. 17 illustrates, diagrammatically, the apparatus of the present invention including, in general terms, the location of various fluid supplies and the location of the optical density reader.

Referring next to FIG. 17, an overall system illustration of the present invention will now be described. The rack 42 is attached to a frame 131 that is movably mounted within housing 132. A motor 133 is provided to shift frame 131 and thus rack 42 laterally so that each column can be positioned above different cells. Furthermore, block 134 is illustrated as mounted to a stepping motor system 162 which moves the block 134 laterally through a drive belt 164. The columns are processed from right to left and from front to back as illustrated in FIG. 17. The cuvettes are processed from left to right and from back to front. To accomplish this, a bar or fence 166 extends across the width of the housing 132, underneath the housing but above the tray 142, and both ends of the bar are connected to a drive mechanism 168. Advancing the drive mechanism 168 moves the bar 166 forwardly such that five cuvettes 24, one from each row, move forwardly clear of the tray 142 and onto a drive mechanism 170. Drive mechanism 170 incudes a pusher block 172 which advances the cuvettes sequentially underneath the mixer needles 154, through the optical reader 156, and thereafter underneath the evacuator needles 158, which are connected through a pump to a waste evacuation system. After the five cuvettes are processed, the mixer needles 154 are cleaned in a wash tray 155 and the evacuator needles 158 are cleaned in a similar wash tray 157 (not shown in FIG. 10). Drive system 168 advances the bar 166 forward, yet another step, such that the next row of five cuvettes may be deposited onto the drive belt 170 and processed sequentially. FIG. 17 also illustrates a cuvette 24a dropping off the drive mechanism after the completion of mixing, reading and evacuation.

After the last cuvette has been processed and removed from the apparatus, the technician attending the apparatus may remove all of the chromatographic columns 10 from the rack 44 and replace them with new ones in preparation for the next cycle of tests. However, economic circumstances may make it preferable to regenerate the columns 10 that have just been used instead. As is known in the art, during regeneration the columns are exposed to chemicals which restore the chromatographic medium in the columns 10 to its original condition. The column analyzer system is configured to permit regeneration without removing the columns 10 from the rack 42 if the columns are being regenerated for immediate re-use. Three regeneration techniques are particularly suitable.

In the first regeneration technique, the technician reloads tray 142 (FIG. 11) with cuvettes 24, and then reinserts the tray 142 in the opening 282 (see FIG. 10) beneath housing 132. The needles are then used to transfer a diluted acid to each of the columns 10, followed by water. After the acid and water drip into the cuvettes 24 beneath the columns, perhaps hastened by applying a low pressure to the columns in the manner previously discussed, the tray 142 is removed and the cuvettes are emptied into a waste receptacle. Fresh cuvettes that will be employed during the next testing run are loaded onto tray 142, which is then inserted into opening 282 before the next testing run is begun.

As an example, assume that the columns 10 have an affinity-type chromatographic media and have just been used during tests in which the specimens were whole blood. In this situation the chromatographic to medium in the columns is contaminated with the sugar sorbitol, which must be removed to restore the medium. The sorbitol can be stripped from the medium using five milliliters of a 0.1 molar concentration of acid, preferably hydrochloric acid, followed by 5 milliliters of water to flush out the acid. The molar concentration of the acid may range from about 0.5 to about 0.05, with 0.1 being recommended. Enough of the acid solution must be used in each column to remove the greatest possible deposit of sorbitol that might be encountered, and this must be followed by enough water to strip any remaining acid from the resin medium.

The tray 142 is not used in the second of the regeneration techniques mentioned above. Instead, after tray 142 has been removed a modified tray 159 (see FIG. 25) is inserted into opening 282 to collect the dilute acid and water which drips through the columns. Tray 159 is open at its top, and includes four walls 161 and a bottom 163. A pipe 165 is connected to bottom 163 at a drain opening (not illustrated) in bottom 163. Bottom 163 is shaped to slope slightly toward the drain opening. Rails 165 are attached to the two walls 161 at the sides of tray 159. The rails 165 slide on corresponding rails (not shown) in the chromatographic apparatus when tray 159 is inserted into opening 182. At the corners between wall 161, tray 159 is sealed with a silicon-based sealant. Although not shown, pipe 165 is connected by tubing to a waste receptacle. After the regeneration procedure the dilute acid and water in the waste receptacle is emptied, and the modified tray is withdrawn from opening 282. A tray 142 of cuvettes can then be inserted to begin a new testing run.

In the third regeneration technique mentioned above, a tray (not illustrated) corresponding to tray 159 is permanently mounted in the chromatographic apparatus, at a position below tray 142. The acid solution and water can then drip into it when tray 142 is removed.

The above-noted regeneration techniques may be used even if the chromatographic columns 10 are to be removed from the system for use at a later date. In this case, after the regeneration procedure the attendant removes the columns 10 from rack 42, installs caps 20, pours in a preservative solution, and then applies caps 12.

It should be further appreciated that as part of the present invention, stepping motor 176 (illustrated diagrammatically in FIG. 17) is provided for driving a cam arrangement such that, at the completion of the chromatographic separation step, rotation of the motor causes raising and lowering the rack 42. This movement causes any drops at the bottom of the tips of the chromatographic columns 10 to drop into the respective cells of the cuvettes 24. This drop removal feature will be described in more detail with reference to FIGS. 18 and 19.

Figure 18:
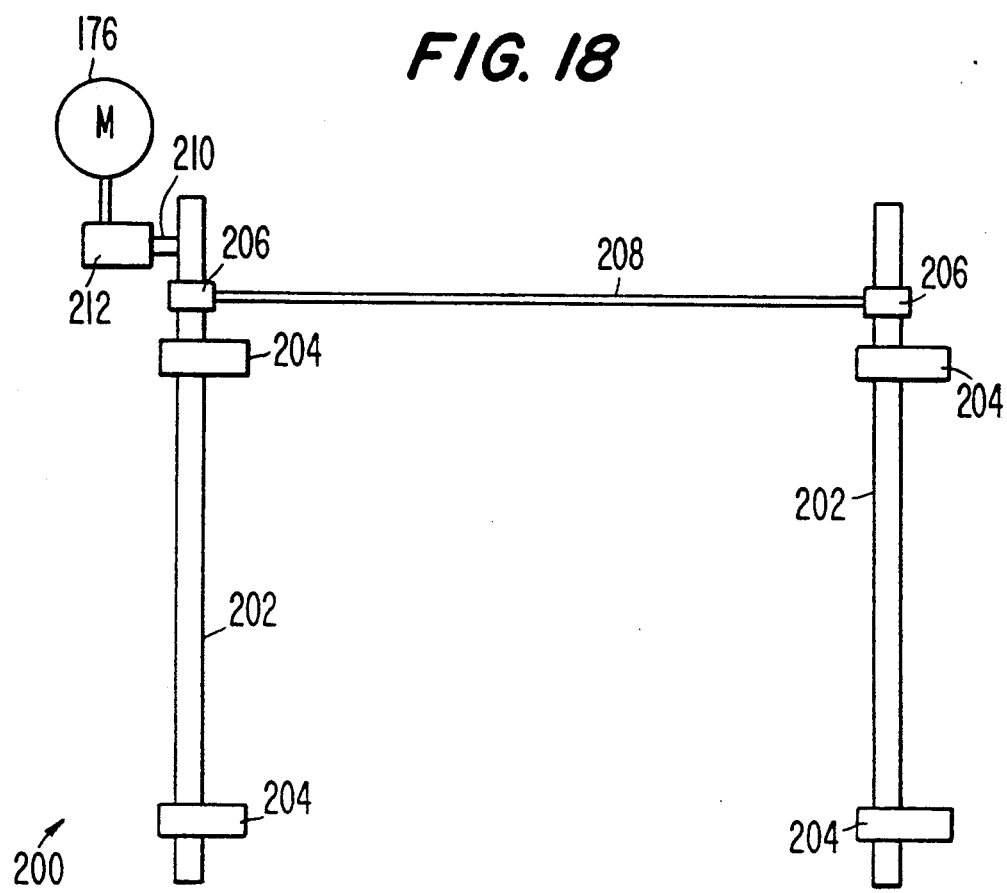
FIG. 18 is a top view schematically illustrating the drop removal mechanism.
Figure 19:
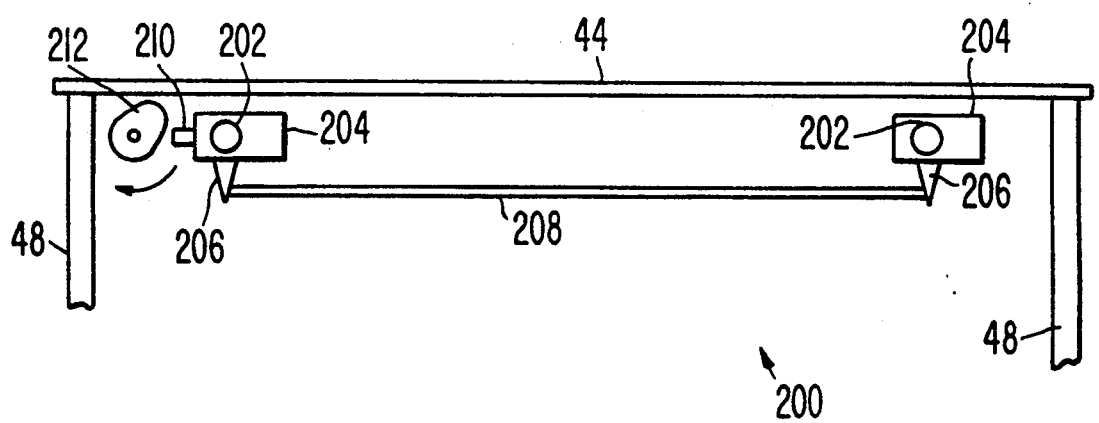
FIG. 19 is a front view of the drop removal mechanism, and shows its cooperation with the top plate of the rack for holding the chromatographic columns.

A top view of drop removal mechanism 200 by itself is shown in FIG. 18, and FIG. 19 illustrates a front view of mechanism 200 in its operative position beneath top plate 44 of rack 42. Mechanism 200 includes a pair of rods 202 which are journaled for rotation beneath plate 44. Rods 202 extend parallel to manifolds 94 (see FIG. 10). Rectangular plastic blocks 204 are attached in an eccentric manner to the rods 202. A block 204 is positioned adjacent each corner of plate 44. Crank members 206 are also attached to bars 202, preferably at a position behind plate 44. Each end of a link 208 is pivotably attached to a crank member 206. Link 208 and crank members 206 cause rods 202 to rotate in unison. Drop removal mechanism 200 also includes a pin 210 affixed to one of the rods 202. Pin 210 is positioned for engagement by a cam 212 which is rotated by stepping motor 176.

Rack 42 normally rests on a support (not illustrated) but is mounted so that it can slide upward slightly from the support. When cam 212 undergoes a clockwise revolution (with respect to FIG. 19), it encounters pin 210 and causes rods 202 to rotate by about 90° before cam 212 separates from pin 210. During this 90° rotation, blocks 204 urge plate 44 and thus rack 42 upward about an eighth of an inch above the support. Rack 42 drops back to the support when cam 212 disengages from pin 210. The resulting jar is sufficient to jiggle loose any drops suspended at the end of the columns 10 supported by the rack 42.

Those skilled in the art will recognize that drop removal mechanism 200 improves the accuracy of the measurements made by the automatic column chromatography machine. During use of the machine fluids are introduced to each column 10 in a sequence, and the eluates from the column are collected in different cells of the cuvette means 24 (FIG. 2). Accuracy would suffer if even a small amount eluate intended for one cell were to contaminate the eluate collected in an adjacent cell. Accordingly, motor cell 176 is actuated to rotate cam 212 by a revolution after each solution has been introduced to the column 10, and before the column is advanced to the next position over an adjacent cell. The result is that the last drop falls into the cell intended instead of the adjacent cell.

The three needles 136, 137, and 138 and the actuating mechanism 139, illustrated in FIG. 10 and in FIG. 17, each move in the "Z" direction under influence of motors. The needles 136, 137, and 138 provide for mixing or agitation of the resin in the columns as well as providing conduits for the addition of reagents and/or samples into the columns. In addition, vertical movement of actuating mechanism 139 (also see FIG. 4) provides for removal of the caps from the columns. Actuating mechanism 139 functions to move spring 60 downwardly.

Reference should also be had to the bellows-motor 180 illustrated in FIG. 17 wherein four bellow systems are shown, each associated with one of the needles 154 and each attached to a motor 182. Motor 182 rotates, and an internal threaded nut system converts the rotation motion of the motor 182 into linear motion of the bellows 180 which, in turn, moves the fluid in the needles 154 vertically for mixing the liquid in the cuvette cells prior to the liquid passing through the optical reader 156.

The bellows-motor arrangement illustrated with respect to the needles or mixer unit 154 may be replicated for movement of the needles 136–139 as they provide controlled, bi-directional movement in small increments.

Figure 20:
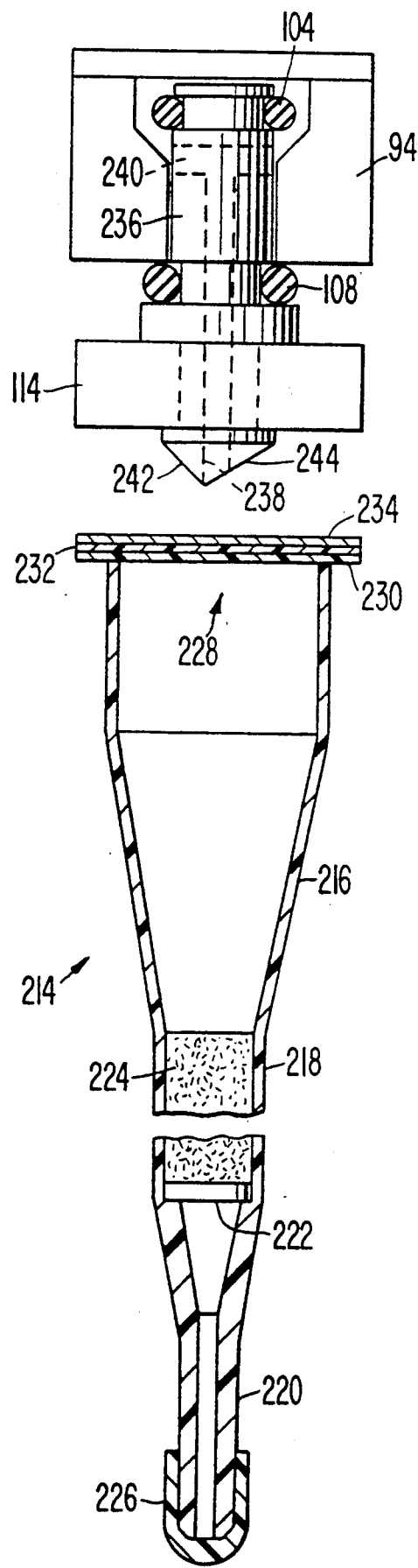
FIG. 20 illustrates a chromatographic column sealed by a foil member in accordance with an embodiment of the present invention, along with a modified embodiment of a pressure tip unit for use with the column.

FIG. 20 illustrates an alternate embodiment for the pressure tip units, and a modified chromatographic column with which it is used. The arrangement shown in FIG. 20 avoids the need to manually unscrew covers 12 (FIG. 1) when the columns are loaded into the rack 42.

In FIG. 20, an improved chromatographic column 214 in accordance with the present invention includes a polypropylene shell which defines a reservoir portion 216, a barrel portion 218 (shown broken away to reduce its length in the drawing), and a tip portion 220. A fluid-pervious disk 222 lodged inside the shell supports a chromatographic medium 224 within barrel portion 218. The medium may be, for example, ion exchange resin particles, affinity resin particles, size-exclusion resins, or matrix-type media such as cellulose, agarose, or silica gel. A removable cap 226 closes the lower end of tip portion 216.

A foil seal member 228 closes the top end of reservoir portion 216. During fabrication of column 214, seal member 228 is fused to the shell using heat (alternatively, adhesive bonding or ultrasonic bonding can be employed). Member 228 includes an adhesion layer 230 of polyethylene which readily fuses with the plastic of the shell. Polypropylene could also be used in layer 230. Layer 230 is bonded to an intermediate layer 232, such as polypropylene. Polyethylene could also be used in layer 232. An aluminum layer 234 is bonded to 232. Layer 232 serves as a moisture barrier. The thickness of layers 230–234 is exaggerated in FIG. 20 for ease of illustration. Layers 230 and 232 are preferably a thousandth or so of an inch thick each. Layer 234 is less than about three thousandths of an inch thick, and preferably about one to two thousandths of an inch thick.

The pressure tip unit that cooperates with column 214 includes a pressure cylinder 236 having three reduced-diameter circumferential recesses machined therein. Cylinder 236 extends movably through a bore in manifold 94. O-rings 104 and 108 are lodged in two of the recesses, and a foam gasket 114 is lodged in the third. An axial bore 238 communicates with a bore 240 across the diameter of cylinder 236. A seal-punching head 242 is provided at the bottom of cylinder 236.

Figure 22:
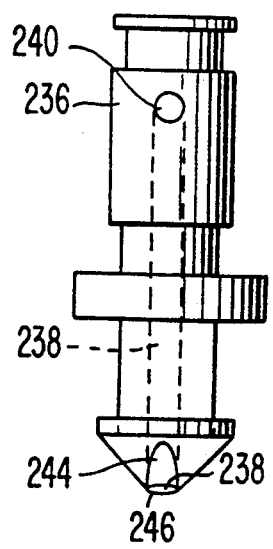
FIG. 22 is a side view of the pressure cylinder in the pressure tip unit of FIG. 20.

During fabrication of pressure cylinder 236, head 242 is initially machined to be conical, with a 90° apex angle (that is, the surface has a 45° angle with respect to the longitudinal axis of cylinder 236). Then one side of head 242 is ground to provide a flat region 244. This leaves a cutting edge 246 (see FIG. 22) along one rim of the bottom opening of bore 238.

During operation up to 50 columns 214 are first loaded into the rack 42. Then motor 160 (FIG. 15) is actuated to move links 152 to the horizontal position as shown in FIG. 16 and thereby lower the manifolds 94. The cutting edges 246 of the pressure cylinders 236 pierce the aluminum layers 234 of the seal members 228, and the continued downward movement of the heads 242 ruptures the seal members 228. Motor 160 is then actuated again to move links 152 to their vertical positions as shown in FIG. 15. Fluids can then be added through the punctured seal members 228 before the manifolds 94 are lowered again to apply pressure to the columns in the manner previously discussed. The aluminum layer 230, being relatively thick, not only provides a secure closure during transportation and handling of the columns 214, it also prevents the ruptured seal member 228 from springing back after the pressure cylinder 236 has been withdrawn. That is, the aluminum remains permanently deformed and prevents the hole formed by head 242 from closing up.

Pressure cylinder 236 can of course replace pressure cylinder 98. An axial blind bore (not shown) can be drilled from the top to hold a spring (not shown) as an aid to closing pressure cylinder 98.

Figure 21B:
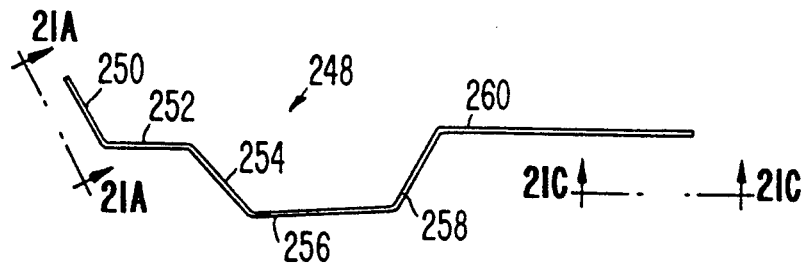
FIGS. 21a, 21b, 21c, illustrates a modified embodiment of the cap removal means with elevation views of each end thereof and with an edge view thereof.
Figure 21A:
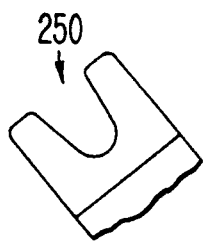
Figure 21C:
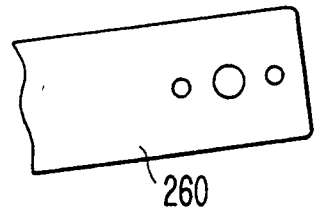

FIGS. 21A-21C illustrate a cap removal means 248 that can be used in lieu of the cap removal means 60 shown in FIGS. 4 and 5A-5C. Cap removal means 248 includes a fork portion 250, intermediate portions 252, 254, 256, and 258, and an end portion 260. Cap removal means 248 is made from a stainless steel strip and cooperates with bearing surface 256 (FIGS. 3 and 4) in the manner previously discussed with respect to cap removal means 60. However, while cap removal means 60 is flexed slightly and acts as a spring during operation, cap removal means 248 is substantially inflexible. Fork portion 250 is preferably 0.34 inches long and has a generally v-shaped slot with a rounded bottom. Intermediate portion 252 is preferably 0.40 inches long and forms an angle of 120° with fork portion 250. Intermediate portion 254 is preferably 0.39 inches long and forms an angle of 135° with intermediate portion 252. Intermediate portion 256 is preferably 0.66 inches long, and forms an angle of 132° with intermediate portion 254. Intermediate portion 258 is preferably 0.37 inches long and forms an angle of 123° with intermediate portion 256. End portion 260 is preferably 1.16 inches and forms an angle of 120° with intermediate portion 158.

FIG. 24 shows cap removal means 248 attached to an actuating mechanism 139' having a flattened lower end 262. Pegs 264 are attached to lower end 262 and extend through the smaller openings in end portion 260 shown in FIG. 21C. A screw 266 extends through the central opening, with the head of screw 266 being spaced apart from the surface of cap removal means 248. A coil spring 268 is disposed around the shaft of screw 266 beneath the head of the screw, and normally biasses portion 260 against flattened lower end 262. However, when actuating mechanism 139' is moved downward in the direction of arrow 270 and portion 254 engages bearing surface 56 (see FIGS. 3 and 4) of rack 42, cap removal means 248 is pivoted about its upper end 272, and fork portion 250 swings in the direction of arrow 274 toward the tip portion 18 (see FIGS. 1 and 4) of a column 10. During further downward motion, portion 256 slides against bearing surface 56 and the cap 20 at the tip of the column is dislodged. When actuating mechanism 139' is later withdrawn, in the direction opposite arrow 270, spring 268 urges cap removal means 248 back to its original position with respect to actuating mechanism 139'. It will be apparent that pegs 264 serve to keep cap removal means 248 aligned, and that pegs 264 are not affixed to cap removal means 248 but are, instead, slightly movable with respect to it.

Spring 268 is shaped like a truncated cone, when seen from the side. Because of this, spring 268 can be flattened so that its coils are nested inside one another. Thus spring 268 can undergo considerably more compression than could a cylindrical spring. Spring 268 is preferably made of stainless steel, with a copper coating to prevent the stainless steel from gauling.

In FIG. 24, actuating mechanism 139' is shown with a rack of teeth 276 for engagement with a gear (not shown) rotated by a motor (not shown) in support block 134 (see FIGS. 10 and 17) to raise or lower actuating mechanism 139'. Actuating mechanism 139 (see FIG. 4) may similarly be provided with a rack of teeth.

Figure 23:
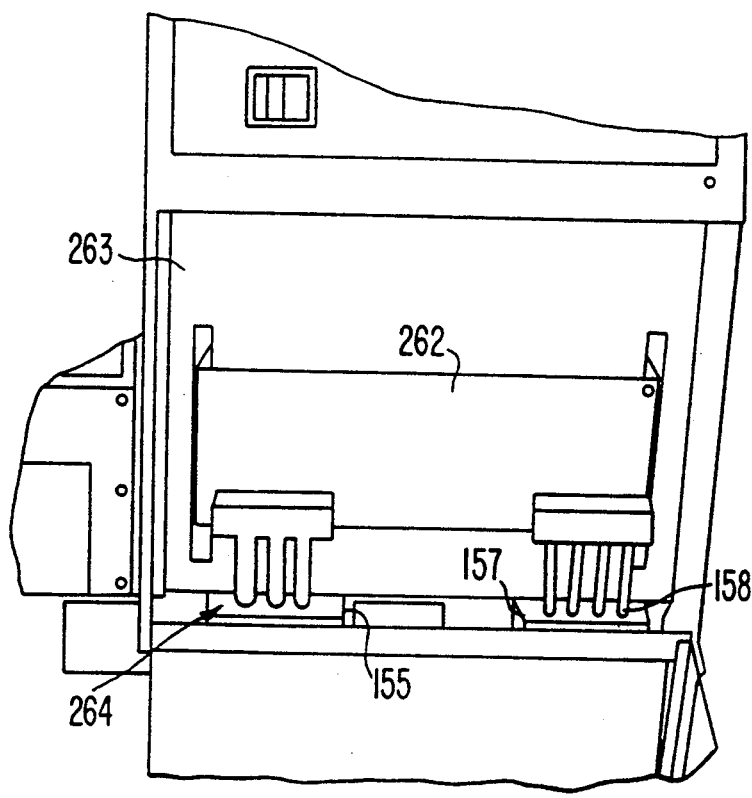
FIG. 23 is a partial front illustration with the door of the apparatus removed, and shows a modification of part of the structure depicted in FIG. 14.

FIG. 23 shows a modification of FIG. 14 which avoids the need for the bellows 180 and motors 182 shown in FIG. 17. In FIG. 23, a plate 262 is mounted on a wall 263 so as to be movable up and down. Wall 263 is movable forward and backward. A paddle assembly 264 with three paddles is mounted on plate 262. The paddles are lowered into cells 38b, 38c, and 38d of cuvette 24 and then moved forward and backward to mix the contents thereof. The paddle for cell 38d is larger than the rest since cell 38d itself is larger than the other cells. A fourth paddle is not needed since the content of cell 38a is not normally read—it contains the cap 20 and a buffer solution that was drained from the column before use. The needles 158 for evacuating the cuvettes are still used. However, the flexible hoses shown leading to the needles 158 in FIG. 14 are diverted behind plate 276 in the embodiment of FIG. 23.

The foregoing is a complete description of a preferred embodiment of the present invention. The invention automates those steps normally performed by a technician in a manual pipetting operation, and the individual steps, per se, are conventional.

Many changes and modifications may be made without departing from the spirit and scope of the present invention. The invention, therefore, should be limited only by the following claims.

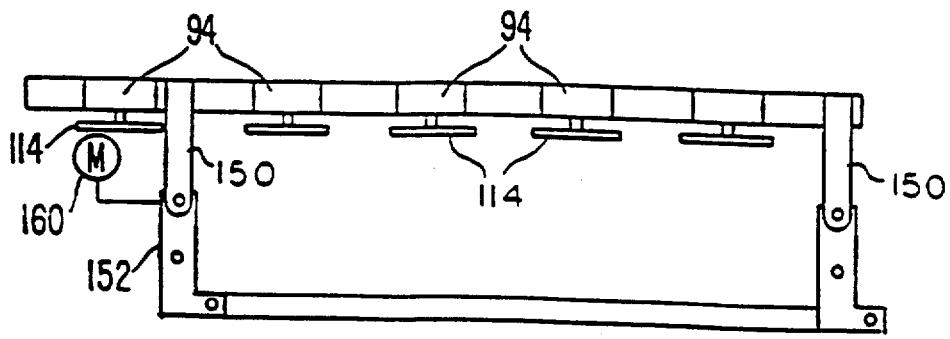

What we claim is:

1. A method for conducting column chromatography, comprising the steps of:
    (a) mounting a chromatographic column having a tip portion in a rack, with the tip portion being directed generally downward;
    (b) introducing a first fluid into the column and collecting a first eluate in a first receptacle that is disposed below the tip portion;
    (c) when step (b) is substantially complete, shaking the rack so as to jar loose any remaining drop of the first eluate, said any remaining drop falling into the first receptacle;
    (d) moving the column above a second receptacle; and
    (e) introducing a second fluid into the column and collecting a second eluate in the second receptacle.

2. The method of claim 1, wherein step (c) is conducted by raising the rack by less than an inch and then dropping it.

3. The method of claim 1, wherein the rack includes a horizontal plate, and wherein step (c) comprises twisting a plurality of rods having blocks attached thereto so as to lift the plate when the rods are twisted.

4. The method of claim 1, wherein a pin is connected to one of the rods, and wherein the step of twisting comprises engaging the pin with a rotating cam.

5. The method of claim 1, further comprising the steps of moving the first and second receptacles to a measuring station, and measuring at least one property of the first and second eluates at the measuring station.

6. The method of claim 5, further comprising the step of simultaneously mixing the first and second eluates with paddles before the measuring step is conducted.

* * * * *

UNITED STATES PATENT AND TRADEMARK OFFICE
CERTIFICATE OF CORRECTION

PATENT NO. : 5,228,988
DATED : 07/20/93
INVENTOR(S) : James R.M. Sanfore, et al

It is certified that error appears in the above-indentified patent and that said Letters Patent is hereby corrected as shown below:

The drawing sheet, consisting of Figure 15, should be deleted to be replaced with the Figure 15, as shown on below.

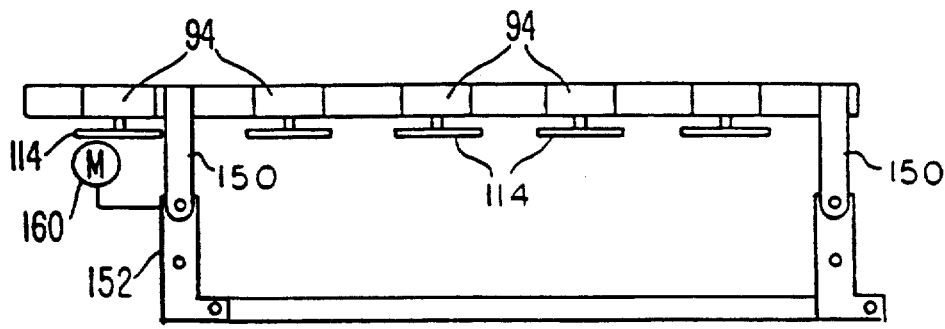

Signed and Sealed this

Third Day of May, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,228,988
DATED : July 20, 1993
INVENTOR(S) : James R. M. Sanford, et. al.

It is certified that error appears in the above-indentified patent and that said Letters Patent is hereby corrected as shown below:

The drawing sheet, consisting of Figure 15, should be deleted to be replaced with the Figure 15, as shown on attached sheet.

This certificate supersedes Certificate of Correction issued May 3, 1994.

Signed and Sealed this

Fourteenth Day of February, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,228,988  Page 2 of 2
DATED : 7/20/93
INVENTOR(S) : James R. M. Sanford, et al It is certified that error appears in the above-indentified patent and that said Letters Patent is hereby corrected as shown below:

FIG. 15